United States Patent [19]

McGregor et al.

[11] Patent Number: 4,524,771
[45] Date of Patent: Jun. 25, 1985

[54] MULTIPLE CURVED SURGICAL NEEDLE

[75] Inventors: Richard C. Troutman, New York, N.Y.; Walter McGregor, Flemington, N.J.

[73] Assignee: Ethicon Inc., Somerville, N.J.; a part interest

[21] Appl. No.: 437,419

[22] Filed: Oct. 28, 1982

[51] Int. Cl.³ ............................................. A61B 17/06
[52] U.S. Cl. .................................... 128/339; 223/102
[58] Field of Search ....................... 128/339, 340, 330; 223/102, 103, 104

[56] References Cited

U.S. PATENT DOCUMENTS

| 1,506,262 | 8/1924 | Slater | 128/339 X |
| 3,197,997 | 8/1965 | Kurtz | 128/339 X |
| 4,011,870 | 3/1977 | Goldstein | 128/340 X |

FOREIGN PATENT DOCUMENTS 862935  9/1981  U.S.S.R. .............................. 128/339

OTHER PUBLICATIONS

"The Fish Hook Needle", McIntyre, M.D., AM. Intra-Occular Implant Soc. J. 6, pp. 282–284 (Jul. 1980).

Primary Examiner—Michael H. Thaler

[57] ABSTRACT

An improved surgical needle. The needle comprises a plurality of curves which provide for improved control while suturing.

11 Claims, 6 Drawing Figures

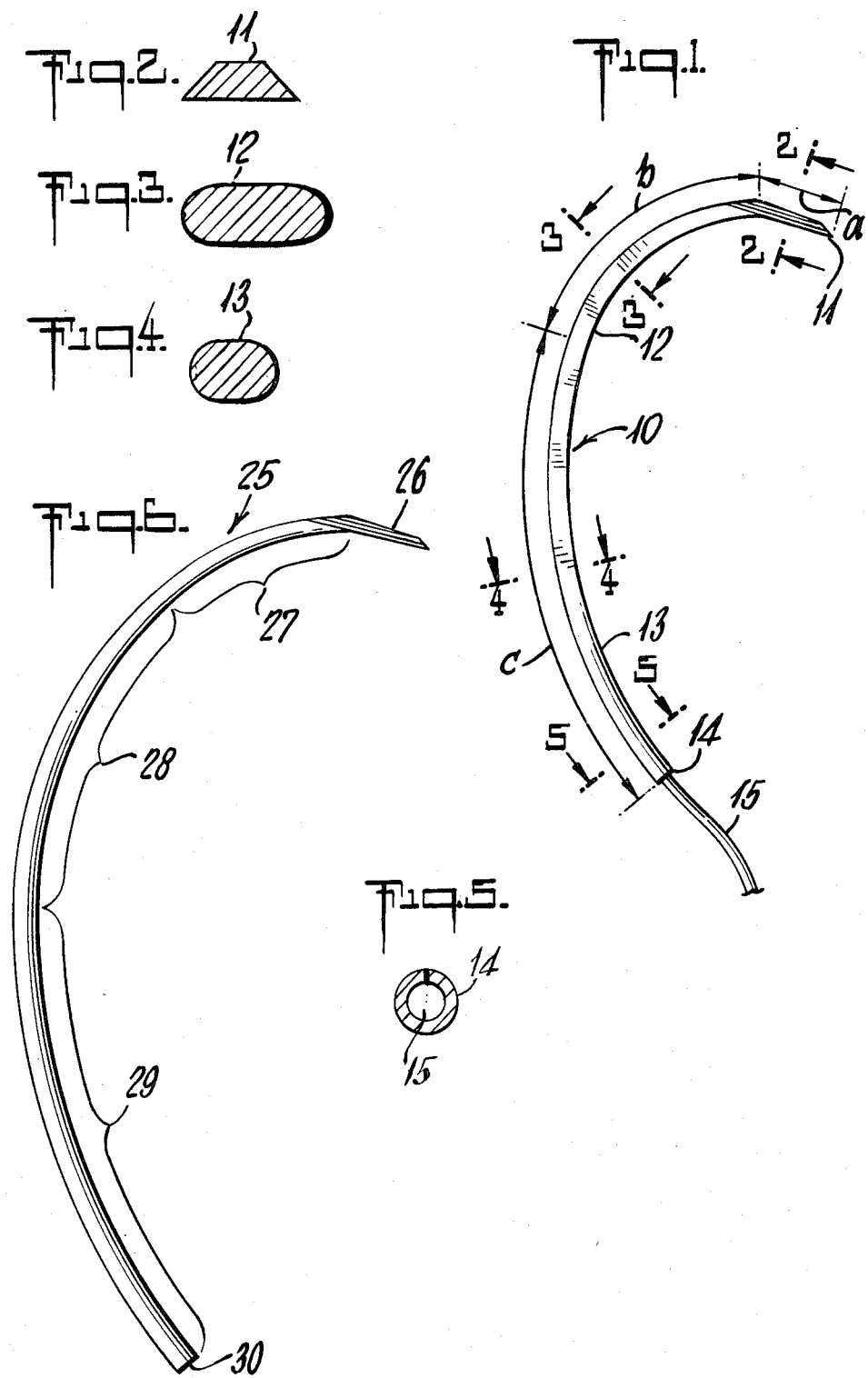

MULTIPLE CURVED SURGICAL NEEDLE

BACKGROUND OF THE INVENTION

The present invention relates to surgical needles and, more particularly, to specifically curved surgical needles for use in ophthalmic surgery, microsurgery and similar surgical procedures.

Surgical needles are generally either straight, ski-shaped, or uniformly curved. For many surgical procedures including eye operations and microsurgery, the curved needles have gained wide acceptance. These needles have a uniform radius and the length of the needle may be from about a quarter of a circle to ⅔rds of a circle; that is, from about 90° to about 240°. The curve in the needle is helpful to the surgeon in placing the suture in that the surgeon usually grasps the body of the needle near its center and inserts the pointed end into the edge of the tissue to be closed. Provided the surgeon keeps a general forward motion along the direction of the shape of the curve of the needle, the needle will tend to place the suture at the desired depth and take the desired "bite" by a controlled emergence of the needle from the tissue. The smaller and more fragile the material being sutured the more difficult it is to suture. Also, the tighter the area in which the surgeon is working, the more difficult it is to suture. These problems are very prevalent in eye surgery. The placing of the suture is critical to success in many eye operations. For example, in a corneal transplant operation, the sutures must be uniformly placed as to depth and length of bite so that the suture loops attain substantially equal tension around the entire transplant circumference. If some sutures have more or less tension than other sutures, or some sutures have been placed at different depths or lengths of bite than others, the results of the operation may not be as successful. Also, the standard curved needle when gripped in the center portion by the needle holder, if gripped too tightly, the area gripped will tend to be straightened. This slight straightening of the center portion increases the difficulty the surgeon has in placing uniform suture loops.

The prior art shows various surgical needle configurations to improve specific suturing techniques. In U.S. Pat. No. 3,556,953 there is disclosed a microminiature suture needle which may be either straight, ski-shaped or curved. In U.S. Pat. No. 3,877,570 there is disclosed a specifically curved needle specifically designed for attaching hair pieces to the human scalp.

Other various shaped surgical needles for improved suturing are described in U.S. Pat. Nos. 3,918,455, 4,128,351, and 4,237,892.

It is also known that a specifically curved needle for opthalmic surgery is being sold for corneal scleral closures by the Alcon Company. This needle is more fully disclosed in an article which appeared in the Am. Intra-Occular Implant Soc. J. 6, 282–284 (1980). Though many of these prior art surgical needles solve some of the problems with regard to the specific procedure for which they were designed, none of them solve all of the problems involved in the suturing techniques required in ophthalmic surgery or in microsurgery or other similar surgical procedures. In ophthalmic surgery, as well as in other surgery, it is important the needle be as sharp as possible. The sharper the needle the less the damage or trauma the needle causes to the tissue being sutured. However, the sharper the needle the less the "feedback" or response the surgeon feels when using the needle and the more difficult for the surgeon to know exactly where the suture is being placed and the depth to which the suture is placed. Also, when the needle is extremely sharp and there is little "feed-back", it is difficult for the surgeon to be certain that each placement of the suture is the same as the previous placement. When using a standard smoothly curved needle in ophthalmic surgery, the surgeon places some torque on the needle to bring the needle appropriately through the tissue. With the desired very sharp needle and, hence, little "feedback", it is very difficult for the surgeon to place the same amount of torque on each placement of the needle and, hence, it is extremely difficult to produce the uniformly tensioned suturing desired in ophthalmic surgery.

What we have discovered is a new and improved surgical needle which reduces the trauma to the patient and provides the needle be placed to the right depth in the tissue and grabs or sutures the right amount of tissue as the suture is being placed. Also, our newly configured needle requires minimal manipulation in placing the suture through the tissue. Furthermore, our newly configured needle allows for improved suturing of fine fragile tissue and allows such suturing to be conducted in very tight and confined places while reducing the possibility of injury to adjacent tissue.

Our new needle may be made as sharp as possible because "feedback" is surprisingly no longer required with our new needle. The specific geometry of our new needle eliminates the requirement of "feedback" because it unexpectedly automatically controls the placement of the suture and surprisingly places each suture in an identical manner. Our new needle has less tendency to be straightened by the needle holder. Our new needle allows for the suturing of delicate corneal tissue accurately and consecutively in a very uniform manner with the desired bite and grasp of the tissue being sutured.

SUMMARY OF THE PRESENT INVENTION

The improved surgical needle of the present invention comprises a multiple curved body portion. The body portion terminates at a blunt end and at a pointed end. The pointed end is straight to provide a self-depth seeking portion. The curve adjacent the pointed end has a radius of curvature of from about 0.040 inch to 0.075 inch and the length of that curvature is from 0.063 inch to 0.105 inch. The curve adjacent the blunt or distal end of the needle has a radius of curvature of from about 0.080 to 0.120 inches and the length of curvature is from 0.081 inch to 0.115 inch. Both curves are in substantially the same concavity. In certain embodiments of the present invention, the two curves abut one another in a smooth manner while in the embodiments of the needle of the present invention there may be a small area of graduated curvature that connects the two critical curves. Though it is necessary that the needle have at least two curves, in certain embodiments of the present invention additional intermediate connecting curves may be used.

In the preferred embodiments of the present invention the needle has a suitable suture swaged or otherwise attached to the blunt end of the needle. In certain embodiments of the present invention the pointed end has a trapezoidal cross-section with the longer parallel side of the trapezoid being on the inside of the curve and the shorter parallel side of the trapezoid being on the outside of the curve. The needle point geometry may also be triangular, taper, taper cut or other geometrics commonly used in surgical needles. The curve adjacent the pointed end has an oval or elliptical cross-section while the curve adjacent the blunt end has a circular cross-section. Other cross-sectional shapes may also be used such as triangular, trapezoidal and the like. Our new and improved needle configuration has a straight point which provides a controlled depth seeking feature when the needle is placed. The initial tight curve provides the relative turnaround desired in ophthalmic or other fine microsurgery and the gentler curve allows for ease of gripping and control of the needle while the suture is being placed. The gentler curve reduces distortion of tissue on withdrawing the needle from the tissue.

Our new needle is gripped by the needle holder closer to the blunt end of the needle. As our new needle has a gentler curve in this area, there is less tendency for the needle holder to straighten the needle.

BRIEF DESCRIPTION OF THE DRAWINGS

The invention will be further described in conjunction with the accompanying drawings wherein:

FIG. 1 is a plan view of the surgical needle of the present invention;

FIG. 2 is a cross-sectional view taken along line 2—2 of FIG. 1;

FIG. 3 is a cross-sectional view taken along line 3—3 of FIG. 1;

FIG. 4 is a cross-sectional view taken along line 4—4 of FIG. 1;

FIG. 5 is a cross-sectional view taken along line 5—5 of FIG. 1; and

FIG. 6 is a plan view of another embodiment of the surgical needle of the present invention.

DETAILED DESCRIPTION OF THE DRAWINGS

Referring to the drawings in detail, FIG. 1 shows a surgical needle 10 of the present invention.

The needle has a straight pointed end 11 having a cross-section as shown in FIG. 2. Adjacent this pointed end is a curved body portion 12 of the needle. The curved body portion has the cross-sectional shape as shown in FIG. 3. Adjacent this curved portion is a second curved portion 13 which is a gentler or less of a curve than the first curved portion. This curved portion of the needle has the cross-sectional shape as shown in FIG. 4. The second gentler curved portion terminates in a blunt or distal end 14 in which preferably a suitable suture 15 is swaged into a drilled hole or a channel or may be attached to the needle by any of the ways well known in the art. The swaged end portion is more clearly shown in FIG. 5.

The straight portion of the needle has a distance 'a' of from about 0.013 to 0.028 inches. We have found 0.021 inch to be most suitable in our new compound curved needles. The straight point cutting blade and the following curvature provide the needle with its self-depth seeking feature so that it will enter the tissue to the desired depth and then curve to place the suture correctly with a minimum of trauma while insuring that a sufficient amount of tissue has been grasped to close the wound. The straight point should be blended or gently curved at a radius of curvature of from 0.010 to 0.020 inch into the body of the needle.

The tighter curve adjacent the pointed end, has a radius of curvature of from about 0.040 to 0.075 inch. We have found a curvature of about 0.055 inch to be most suitable. The length 'b' of this curve is preferably from about 75 degrees to 90 degrees. We have found approximately an 80° length of the angle of this curve to be most suitable.

The gentler curve adjacent the blunt end of the needle has a radius of curvature of from 0.080 inch to 0.120 inch. We have found a curvature of 0.100 inch to be most suitable. The length 'c' of this curve is preferably from about 40 to 60 degrees with 45° being most acceptable.

The two curves may abut each other as shown in FIG. 1 or if desired there may be a short gradually curved area between the two curves to provide for an even smoother transition from one curve to the other.

The needle may be made from any of the materials used in surgical needles although the preferred material is stainless steel. We have found that stainless steel wire having a diameter of from 0.003 inch to 0.017 inch to be most suitable in making needles of the present invention. The needles are manufactured by any of the techniques well known in the art.

As may be seen in the cross-sectional views of FIGS. 3 and 4, our new needle is flattened more than ⅔rds of the distance from the pointed end towards the blunt end. Our new needle is meant to be gripped by the needle holder approximately where the center ⅓ and the distal ⅓ of the needle meet; i.e., in the gentler curved portion of the needle. By gripping in the gentler curved portion there is less possibility of straightening the needle caused by gripping the needle too tightly. Also, because our new needle is meant to be gripped close to the blunt end of the needle, the overall needle length may be reduced and consequently the tissue trauma caused by the needle is reduced.

Referring to FIG. 6 there is shown another embodiment of the surgical needle of the present invention. In this embodiment, the needle 25 has a straight pointed end 26. Adjacent this pointed end is a first curved body portion 27 and adjacent this first curved body portion is a second curved body portion 28. The radius of curvature of both these curves is between 0.040 inch and 0.075 inch and the total length of these curves should be between 0.063 inch and 0.105 inch. A third curved portion 29 is adjacent the blunt end 30 of the needle. By using these multiple curves you are able to obtain even greater control in the use of the needle in certain instances.

Any of the standard absorbable or nonabsorbable sutures may be used with the surgical needles of the present invention. The preferred absorbable sutures may be made from catgut or lactide and/or glycolide polymers and copolymers. The preferred non-absorbable sutures may be made from silk, nylon polypropylene, or the polyesters.

The surgical needles of the present invention may be sterilized by any of the well known techniques such as ethylene oxide, irradiation, etc. and are placed in suitable suture holding packets to provide sterile packaging as is well known in the art.

In use, the needle is gripped by a needle holder at the juncture of the middle and distal thirds of the needle. The straight pointed end of the needle is directed vertically at the tissue to be penetrated. The vertical position is maintained until the desired tissue depth is reached. The needle is abruptly turned (approximately 90 degrees) so that the point assumes a horizontal trajectory and the needle passed through the tissue. The needle is then turned approximately another 90 degrees so that it exits vertically on the opposite side of the incision thereby establishing the bite the suture has taken.

The needles of the present invention may be manufactured by any of the methods well-known in the art of needle manufacture. A preferred method for manufacturing the needles of the present invention is to first straighten a length of wire from a coil. The diameter of the wire may be 4 mil, 6 mil or other diameter as desired. The straightened wire is cut to length as is well-known to provide a cut piece of straight wire. One end of the straight wire is ground by standard techniques to provide a tapered configuration and a generally pointed end. The unground end or blunt end is treated to provide a means for attaching a suture material to that end. This treatment may comprise drilling the end of the needle to provide a hole in the end as is well-known. The treatment may also comprise placing a channel in this end portion as is known. In certain embodiments of the method of the present invention, longitudinal portions of the wire are flattened to provide a generally oval cross-section at this flattened portion to aid in handling the needle during the surgical procedure. Also in this forming step the tapered end of the wire may be provided with a triangular, trapezoidal or similar cross-sectional shape as desired. The edges of the formed configuration may be further ground to provide sharp cutting edges in the formed portion.

The wire is then bent to place a plurality of curves in the wire. This is accomplished by a continuous bending operation wherein the curve adjacent the unground end or blunt end of the wire is placed first and then the bending operation continued to place the curve adjacent the pointed end in the wire. It is important to the present invention that the gentler curve be placed in the wire first and then the tighter curve be placed in the wire and that the curves be placed in the wire in a continuous operation; for example, by bending the wire around a mandrel whose surface contains the desired curves. It is believed that by placing the curves in the wire as described and in a continuous operation produces a smooth transition from one curve to the next which is important in order to provide a uniform, smooth needle which can be used and causes a minimum of trauma to tissue. The straight point at the ground end of the wire is placed in the wire by continuing to bend the wire about the mandrel. Appropriate suture material is attached to the unground end of the wire as is well-known.

If longitudinal portions of the needle are flattened to aid in the handling of the needle by an appropriate instrument during the surgical procedure, these flattened areas should be on the inside of the curve and the outside of the curve.

Because the needles are made of steel or similar springy materials, the mandrel used should have tighter curves than those desired in the final needle to allow for some springback after the bending operation. In some embodiments of the method of the present invention where the suture material must be placed in a straight portion of the needle, a short portion of the left straight until the suture material is attached and that short portion then bent to the appropriate gentler curve. Also in various embodiments of the present invention the wire may also be heat treated and/or electropolished as is well-known in the art.

Clearly, various other modifications in the described invention may be made without departing from the spirit of the invention and the foregoing description is to be considered merely exemplary and not in the limiting sense. The scope of the invention is indicated by reference to the following claims.

What is claimed is:

1. A surgical needle comprising a multiple curved body portion terminating in a blunt end and a stra-ght point end, all curves of the multiple curves being concave, the curve adjacent the pointed end of the needle having a radius of curvature of from 0.040 inch to 0.075 inch and a length of curvature of from 0.063 inch to 0.105 inch, and the curve adjacent the blunt end of the needle having a radius of curvature of from 0.080 inch to 0.120 inch and a length of curvature of from 0.081 inch to 0.115 inch the axis of said straight point end intersecting at an angle the concavity of said concave curve adjacent said straight point end whereby the straight point provides a controlled depth during the placement of the needle, the tighter initial curve provides the desired turnaround of the needle when the needle is placed and the gentler curved portion provides ease of gripping of the needle and control of the needle during placement.

2. A needle according to claim 1 wherein the curve adjacent the pointed end of the needle is in abuting relationship with the curve adjacent the blunt end of the needle.

3. A surgical needle comprising a multiple curved body portion terminating in a blunt end and a straight point end, all curves of the multiple curves being concave, the curve adjacent the pointed end of the needle having a radius of curvature of from 0.040 inch to 0.075 inch, a length of curvature of from 0.063 inch to 0.105 inch and an angle of curvature of from 75 degrees to 90 degrees, and the curve adjacent the blunt end of the needle having a radius of curvature of from 0.080 inch to 0.120 inch, a length of curvature of from 0.081 inch to 0.115 inch and an angle of curvature of from 40 degrees to 60 degrees the axis of said straight point end intersecting at an angle the concavity of said concave curve adjacent said straight point end whereby the straight point provides a controlled depth during the placement of the needle, the curve adjacent the pointed end of the needle provides the desired turnaround of the needle when the needle is placed and the curve adjacent the blunt end of the needle provides ease of gripping of the needle and control of the needle during placement.

4. The needle of claim 1, 2 or 3 wherein a suture is swaged to the blunt end of the needle.

5. A needle according to claim 4 wherein the straight pointed end of the needle has a trapezoidal cross-section with the longer parallel side of the trapezoid being on the inner curve of the needle and the shorter parallel size of the trapezoid being on the outer curve of the needle.

6. A needle according to claim 4 or 5 wherein the curve adjacent the pointed end of the needle has a generally oval cross-section and the curve adjacent the blunt end of the needle has a generally circular cross-section.

7. A needle according to claim 6 having flattened sides extending at least ⅔rds of the distance from the straight point towards the blunt end whereby said needle may be gripped by a needle holder substantially closer to said blunt end than to said straight point.

8. A surgical needle according to claim 1 wherein the curve adjacent the pointed end of the needle has a radius of curvature of 0.055 inch and the curve adjacent the blunt end of the needle has a radius of curvature of 0.100 inch.

9. A surgical needle according to claim 3 wherein the curve adjacent the pointed end of the needle has an angle of curvature of 80° and the curve adjacent the blunt end of the needle has an angle of curvature of 45°.

10. A surgical needle according to claims 4, 5, 8 or 9 wherein the length of the pointed end of the needle is from 0.013 inch to 0.028 inch.

11. A surgical needle according to claim 10 wherein the length of the pointed end of the needle is 0.021 inch.

* * * * *

UNITED STATES PATENT AND TRADEMARK OFFICE
CERTIFICATE OF CORRECTION

PATENT NO. : 4,524,771
DATED : June 25, 1985
INVENTOR(S) : Richard C. Troutman, et al It is certified that error appears in the above-identified patent and that said Letters Patent is hereby corrected as shown below:

On the title page:

Item [19], "McGregor et al." should read
--Troutman et al.--

*Signed and Sealed this*

Sixth *Day of* August 1985

[SEAL]

*Attest:*

DONALD J. QUIGG

*Attesting Officer*  *Acting Commissioner of Patents and Trademarks*